United States Patent [19]

Zobrist et al.

[11] Patent Number: 4,963,545

[45] Date of Patent: Oct. 16, 1990

[54] BENZOTHIAZEPINE ANTI-SEIZURE METHOD

[75] Inventors: Ray H. Zobrist; William R. Morrone, both of Olathe, Kans.

[73] Assignee: Marion Laboratories, Inc., Kansas City, Mo.

[21] Appl. No.: 440,376

[22] Filed: Nov. 22, 1989

Related U.S. Application Data

[63] Continuation-in-part of Ser. No. 198,054, May 24, 1988, Pat. No. 4,879,289.

[51] Int. Cl.$^5$ ............................................. A61K 31/55
[52] U.S. Cl. .................................................... 514/211
[58] Field of Search .......................................... 514/211

[56] References Cited

U.S. PATENT DOCUMENTS

| | | | |
|---|---|---|---|
| 3,075,967 | 1/1963 | Krapcho | 540/491 |
| 3,562,257 | 2/1971 | Kugita et al. | 540/491 |
| 3,895,006 | 7/1975 | Krapcho et al. | 540/491 |
| 3,983,106 | 9/1976 | Krapcho et al. | 540/491 |
| 4,567,175 | 1/1986 | Takeda et al. | 540/491 X |
| 4,879,289 | 11/1989 | Zobrist et al. | 514/211 |
| 4,885,375 | 12/1989 | Wynberg et al. | 549/557 |

OTHER PUBLICATIONS

Porter et al., Cleve. Clin. Q.; 51, pp. 293–305 (1984).

*Primary Examiner*—Stanley J. Friedman
*Attorney, Agent, or Firm*—Christopher John Rudy

[57] ABSTRACT

Seizures are ameliorated with certain benzothiazepines.

15 Claims, No Drawings

BENZOTHIAZEPINE ANTI-SEIZURE METHOD

This is a continuation-in-part of PCT/U.S. 89/02220 filed May 23, 1989, which continues Ser. No. 07/198,054 filed May 24, 1988, U.S. Pat. No. 4,879,289 (Nov. 7, 1989), incorporated herein by reference.

FIELD

This invention concerns seizure treatment.

BACKGROUND

Zobrist et al., U.S. patent application Ser. No. 70/198,054 filed May 24, 1988, U.S. Pat. No. 4,879,289 (Nov. 7, 1989), discloses a method of ameliorating epileptic seizures. That invention in summary is a method of ameliorating generalized tonic-clonic type epileptic seizures in a mammal by systemically administering to a mammal in need of such treatment a compound having calcium antagonist activity and the formula:

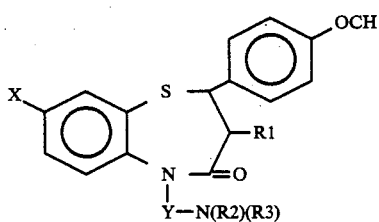

(I)

wherein X is hydrogen, a lower straight chain or branched alkyl, hydroxy, a halogen or a lower straight chain or branched alkyl halide; Y is a lower straight chain or branched alkyl; R1 is hydrogen, hydroxy or acetyloxy; R2 and R3 are each a lower straight chain or branched alkyl or a non-aromatic saturated or unsaturated cycloalkyl having no more than 6 carbon atoms or together are a heterocyclic, and pharmaceutically acceptable salts thereof.

The art lacks and needs further methods for ameliorating such seizures.

SUMMARY

This invention provides a method for ameliorating a generalized tonic-clonic type epileptic seizure in a mammal comprising systemically administering to a mammal in need of treatment therefor a Benzothiazepine-compound in an amount effective to ameliorate said seizure.

The invention is useful in seizure treatment.

Notably, the present invention provides a further method for ameliorating such a siezure as aforesaid. The treatment it provides can be unexpectedly effective.

Further advantages attend this invention as well.

ILLUSTRATIVE DETAIL

The terms "ameliorating" or "ameliorate" refer herein to improving or improvement by reduction or termination of the seizure condition of the mammal. It refers to all degrees of improvement, also including prevention.

The term "generalized tonic-clonic type epileptic seizure" refers herein to the usual or composite form especially denoting a symptom complex characteristic of a class or the like of a bilaterally symmetrical convulsion, without local onset, of a tonoclonic, i.e., of both a tonic and a clonic, nature, which is a state of continuous, unremitting muscular contraction followed by repetitive contraction and relaxation, i.e., jerking, symptiomatic of a chronic disorder characterized by paroxysmal attacks of brain dysfunction due to excessive neuronal discharge, and usually associated with some alteration of consciousness. However, as such, the term is intended to represent a diagnosis classification approved by the International League Against Epilepsy in September of 1981. See e.g., Porter et al., *Cleve. Clin. Q.*, 51 293-305 (1984).

The term "systemically administering" refers herein to applying or giving to the organism entirely as distinguished from any of its individual parts. As such, systemically administering of the Benzothiazepine-compound can be generally accomplished by such methods as, for example, oral ingestion of an oral or sublingual dosage form such as a tablet, capsule, bead sample, syrup, elixer, dragee, and so forth and the like, injection of an injectable solution or suspension, application of a transdermal or other external preparation such as a solution, creme, gel or other ointment, and/or insertion of a rapid or sustained release device.

The term "mammal" refers herein to an animal of the class Mammalia. The mammal can be a human being.

The term "need of treatment therefor" refers herein to a condition requiring management or relief for the generalized tonic-clonic type epileptic seizure included are posterior, prohpylactic and/or palliative treatment(s).

The term "Benzothiazepine-compound" refers herein to a benzothiazepine-type compound, and to pharmaceutically acceptable salt(s) thereof, having calcium antagonist activity and which is represented by the following general formula:

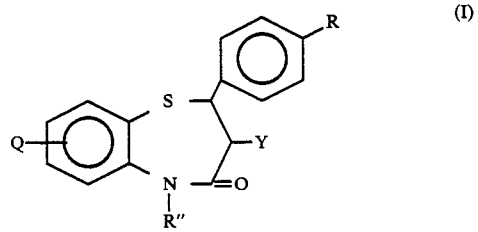

(I)

wherein

Q is hydro (H) or halo to include fluoro (F) and chloro (Cl), especially H or 8-Cl;

R is H, lower alkoxy, lower haloalkyl, cyano (CN), lower alkyl to include methyl (CH3) or halo to include F & Cl, especially H, methoxy (OMe), trifluoromethyl (CF3) or CN;

Y is

OR', wherein R' is H or alkylacyl to include, e.g., lower alkylacyl and adamantylcarboxy, etc., especially H, or lower alkylacyl to include groups such as acetyl, propionyl, butyryl, pivalyl, valeryl, isovaleryl, etc., provided that then there is full saturation between carbons 2 & 3 of the benzothiazepine nucleus and 2,3-dihydrofunctionality thereat as well, or Cl, provided that then there is ethylenic unsaturation between positions 2 & 3 of the benzothiazepine nucleus, and R" is 2-[di(lower alkyl)amino]ethyl (R"1), 3-[di(lower alkyl)amino]propyl (R"2), 2-(pyrrolidino)ethyl (R"3), 3-(pyrrolidino)propyl (R"4), 2-piperidino)ethyl (R"5), 3-(piperidino)propyl (R"6), 2-(morpholino)ethyl (R"7), 3-(morpholino)propyl (R"8) or (N-pyridinium)alkyl with a suitable counterion being present (+R"9-X), especially R"1, e.g., with R"1· being 2-(dimethylamino)ethyl (R"1a) or with R"1 being 2-(diisopropylamino)ethyl (R"1b), or R"3, or R"5, or +R"9-X, e.g., with +R"9-X being 2-(N-pyridinium)ethyl with a bromide and/or chloride counterion being present (+R"9a-X),
provided that, in the cis-configuration, when Q is H or 8-Cl, R is methoxy, R' is acetyl, and R" is R"1a, the compound is the levorotary isomer.

Generally, with respect to the 2,3-dihydro compounds, the cis-configuration, i.e., about positions 2 & 3 of the benzothiazepine nucleus, is or can be present, with some exceptions to this, e.g., as aforesaid and also preferably with the trans-configuration, i.e., about positions 2 & 3 of the benzothiazepine nucleus, being present in the cases of Q being H or 8-Cl, R being methoxy, R' being H, and R"being R"5. Also generally, if the compound has a chiral carbon, racemates or separate optical antipodes may be present in the practice of this invention, with some exceptions to this, e.g., the levorotary optical antipodes corresponding to diltiazem and to d-cis-TA3090 being two such exceptions.

Suitable pharmaceutically acceptable salts generally sulfate, the citrate, and so forth.

The Benzothiazepine-compounds can be made by reacting a suitable glycidic acid ester with a suitable aminothiophenol to prepare corresponding aminophenylthiopropionic acid ester, then cyclyzing the latter ester or its corresponding free acid, followed by N-alkylation and 3-acylation as may be desired. See e.g., Kugita et al., U.S. Pat. No. 3,562,257 (Feb. 9, 1971); Takeda et al., U.S. Pat. No. 4,567,175 (Jan. 28, 1986); Borcherding et al., U.S. patent application Ser. No. 07/440,383 entitled, "BENZOTHIAZEPINES," and filed on even date herewith; Wynberg et al., Ser. No. 07/195,749, now issued as U.S. Pat. No. 4,885,375 (Dec. 5, 1989); Wynberg et al., U.S. patent application Ser. No. 07/439,678 entitled, "GLYCIDIC ACID ESTERS BY BAEYER-VILLAGER REARRANGEMENTS," and filed on even date herewith; Martin, U.S. patent application Ser. No. 07/440,377 entitled, "CYANO ESTERS AND AZEPINONES," and filed on even date herewith, and Martin, U.S. patent application Ser. No. 07/400,658 filed Aug. 31,1989, each of these being incorporated herein by reference. In addition, the Benzothiazepine-compounds having the vinyl chloride at positions 2 & 3 of the benzothiazepine nucleus can be made by processes known in the art. See e.g., Krapcho et al., U.S. Pat. No. 3,895,006 (Jul. 15, 1975); Krapcho et al., U.S. Pat. No. 3,983,106 (Sept. 28, 1976); Krapcho, U.S. Pat. No. 3,075,967 (Jan. 29, 1963), each of these being incorporated herein by reference.

The term "an amount effective" refers herein to an effective amount, which is any amount necessary to at least ameliorate, or optimally completely control or prevent, the seizures. For example, in human patients in general, effective amounts can be about from 0.1 to 300 mg of Benzothiazepine-compound administered per day.

The following further illustrates this invention.

EXAMPLE

All compounds were dissolved in deionized water and administered at a dose from 0.1 milligram (mg) per kilogram (kg) of mammal weight to 100 to 300 mg per kg of mammal weight. Each sample, or control, was administered by interperitoneal injection in a volume of liquid equal to 10 microliters (uL) of the liquid per g of mammal weight. Each mammal was a male CF-1 mouse (Charles Rivers Breeding Laboratories) weighing an average of 25 g. One hour after the injection, the mouse was tested. In general, rotorod toxicity (RT), maximal electroshock seizure (MES) and subcutaneous pentylenetetrazole seizure threshold (scMET) tests were carried out, without administration of anesthesia as anesthetic agents may have interfered with seizure development and therefore masked any beneficial actions of the administered compounds, as follows.

The RT test, designed to detect a minimal neurological deficit from acute compound-induced toxicity in the mouse, required that the mouse was placed on a 1-inch (2.54 cm) diameter knurled plastic rod rotating at 6 rotations per minute (rpm). Neurological deficit, e.g., ataxia, sedation, hyperexcitability, was indicated by the inability of a mouse to maintain equilibrium on the rotating rod for at least 1 minute in each of 3 trials, normal mice able to remain indefinitely on the rotating rod.

Data from the RT test was used to calculate, by probit analysis, the dose at which 50 percent of mice would fail the RT test. This was considered a toxic dose for half of a sample of mice, i.e., TD50, in dose units, i.e., in units of mg per kg.

The MES test, designed to elicit maximal seizure in all normal mice, required that a 60 Hertz (Hz) alternating current (AC) of 50 milliamperes (mA), 5 to 7 times that necessary to elicit minimal seizure, was delivered by corneal electrodes for 0.2 seconds. A drop of 0.9 weight percent aqueous sodium chloride solution was applied to each eye of the mouse, and the electrical stimulus was applied. The mouse was restrained by hand and released at the time of stimulation in order to visually observe the entire seizure, which typically lasted for approximately 22 seconds and was characterized by a short period of initial tonic flexion followed by a prolonged period of tonic extension, especially of the hind legs, and finally a short period of terminal clonus. Elimination of the hind-leg tonic-extensor component, i.e., hind-leg tonic extension that did not exceed a right angle to the trunk of the body, indicated that the compound can prevent MES-induced seizure spread, and therefore, failure of the mouse to extend its hind limbs to an angle with the trunk of the body greater than the right angle was defined as protection.

Data from the MES test was used to calculate, by probit analysis, the dose at which 50 percent of mice would be protected in the MES test. This was considered an effective dose for half of a sample of mice, i.e., ED50, in dose units, i.e., in units of mg per kg.

A therapeutic index (TI) can be calculated by dividing the TD50 by the ED50. The TI is indicative of a margin of safety of a drug such that the higher the TI of a drug, the safer it is.

The scMET test, designed to produce threshold or minimal (olonio) seizures, required the subcutaneous administration of METRAZOL, as a solution of 0.85 weight percent METRAZOL in 0.9 weight percent aqueous sodium chloride solution, in a loose fold of skin on the back of the neck of the mouse in a dose of 85 mg per kg. The mouse was observed for seizures for 30 minutes after the METRAZOL administration, during which time characteristic clonic seizures are produced in approximately 98 percent of normal mice. The absence of a single 5 second episode of clonic spasms, a threshold seizure, was defined as protection.

Table I identifies compounds tested, with substituent references being made to the formula I. Note that the compounds are specifically identified in terms of particular isomers or configurations. However, analogous compound nomenclature without such specific identification refers to all isomeric homologs of that compound. Table II lists results, with dose units being mg per kg.

TABLE I

| Compound | Q | R | Y: R' of OR' & C | R" | Salt |
|---|---|---|---|---|---|
| l-cis-DTZ | H | OMe | acetyl | R"1a | HCl |
| l-cis-TA3090 | 8-Cl | OMe | acetyl | R"1a | maleate |
| d-cis-ML1013 | H | OMe | valeryl | R"1a | fumerate |
| d-cis-ML1014 | H | OMe | isovaleryl | R"1a | fumerate |
| d-cis-ML1015 | H | OMe | pivalyl | R"1a | fumerate |
| d-cis-ML1016 | H | OMe | acetyl | R"1b | HCl |
| dl-cis-ML1017 | H | OMe | H | R"5 | HCl |
| dl-cis-ML1018 | H | OMe | acetyl | R"5 | HCl |
| dl-cis-ML1020 | H | OMe | H | R"3 | HCl |
| dl-cis-ML1021 | H | OMe | acetyl | R"3 | HCl |
| dl-cis-ML1047 | 8-Cl | OMe | pivalyl | R"1a | fumerate |
| dl-cis-ML1048 | H | OMe | H | R"6 | HCl |
| dl-cis-ML1063 | H | OMe | H | R"7 | HCl |
| dl-cis-ML1064 | H | OMe | acetyl | R"7 | HCl |
| dl-cis-ML1065 | H | OMe | H | +R"9a-X | Br/Cl |
| dl-cis-ML1066 | H | OMe | acetyl | +R"9a-X | Br/Cl |
| dl-cis-ML1077 | H | Cl | H | R"1a | HCl |
| dl-cis-ML1078 | H | CF3 | H | R"1a | HCl |
| dl-cis-ML1079 | H | Me | H | R"1a | HCl |
| dl-cis-ML1080 | H | OMe | adamantylcarboxy | R"1a | fumerate |
| dl-cis-ML1082 | H | CF3 | H | R"5 | HCl |
| dl-trans-ML1096 | 8-Cl | OMe | H | R"5 | HCl |
| ML1097 | H | OMe | *Cl | R"1a | HCl |
| dl-cis-ML1098 | H | H | H | R"5 | HCl |
| dl-trans-ML1103 | H | OMe | H | R"5 | HCl |
| dl-cis-ML1104 | H | CN | H | R"5 | HCl |

*vinyl chloride at position 2,3

TABLE II

| Compound | MES protection @ Dose | ED50 | TD50 | TI | scMET |
|---|---|---|---|---|---|
| l-cis-DTZ | 50% (5/10) @ 100 | | | | None |
| l-cis-TA3090 | 40% (2/5) @ 100 | | | | None |
| d-cis-ML1013 | 0% (0/8) @ 100 | | | | None |
| d-cis-ML1014 | 20% (2/10) @ 100 | | | | None |
| d-cis-ML1015 | 0% (0/9) @ 100 | | | | None |
| d-cis-ML1016 | 89% (8/9) @ 100 | | | | None |
| dl-cis-ML1017 | 100% (10/10) @ 100 | | | | None |
| dl-cis-ML1018 | 90% (9/10) @ 100 | 45.6 | | | None |
| dl-cis-ML1020 | 70% (7/10) @ 100 | | | | None |
| dl-cis-ML1021 | 89% (8/9) @ 100 | 76.1 | 97.5 | 1.3 | None |
| dl-cis-ML1047 | 0% (0/9) @ 100 | | | | None |
| dl-cis-ML1048 | 0% (0/9) @ 100 | | | | None |
| dl-cis-ML1063 | 20% (2/10) @ 100 | | | | None |
| dl-cis-ML1064 | 20% (2/10) @ 100 | | | | None |
| dl-cis-ML1065 | 0% (0/8) @ 100 | | | | None |
| dl-cis-ML1066 | 0% (0/4) @ 100 | | | | None |
| dl-cis-ML1077 | 100% (10/10) @ 100 | 55.7 | | | None |
| dl-cis-ML1078 | 100% (10/10) @ 100 | 13.4 | 84.5 | 6.3 | None |
| dl-cis-ML1079 | 50% (5/10) @ 100 | | | | None |
| dl-cis-ML1080 | 0% (0/5) @ 100 | | | | None |
| dl-cis-ML1082 | 100% (12/12) @ 100 | 23.7 | | | None |
| dl-trans-ML1096 | 30% (3/10) @ 100 | 87.2 | 203.1 | 2.3 | None |
| ML1097 | 90% (9/10) @ 100 | 47.7 | 125.2 | 2.6 | None |
| dl-cis-ML1098 | 0% (*0/10) @ 100 | | | | None |
| dl-trans-ML1103 | 100% (10/10) @ 100 | | | | None |
| dl-cis-ML1104 | 20% (1/5) @ 100 | | | | None |

*100% death at this dose

In conjunction with Table II, the following salient data was collected and is listed as follows. The list employs the following format: Benzothiazepine-compound as identified in Table I: Dose, in mg per kg, test, i.e., RT (number not having observed deficit/number tested, plus any comments) and MES (number protected/number tested, plus any comments).

d-cis-ML1016 30, RT (0/5) MES (0/5); 60, RT (0/5) MES (1/5); 100, RT (0/4, 1 died) MES (¾, 1 died).

dl-cis-ML1017: 3, RT (0/10) MES (0/10); 10, RT (0/14) MES (0/14); 30, RT (0/14) MES (0/14); 100, RT (9/9) MES (9/9); 200, (4 tested, and 4 died).

dl-cis-ML1018: 30, RT (0/11) MES (1/11); 60, RT (1/5) MES (4/5); 100, RT (4/4) MES (4/4).

dl-cis-ML1021: 30, RT (0/5) MES (0/5); 60, RT (0/5) MES (1/5); 80, RT (2/5) MES (3/5); 100, RT (2/5) MES (4/5); 120, RT (3/3, 2 died) MES (½); 140, RT (1/1, 4 died) MES (1/I, 4 died); 200, RT (1/1, 4 died) MES (1/1, 4 died).

dl-cis-ML1048: 10, RT (0/4) MES (0/4); 30, RT (0/4) MES (¼); 60, RT (¼) MES (3/3); 100, RT (3/3) MES (3/3).

dl-cis-ML1077: 10, RT (0/4) MES (0/4); 30, RT (0/4) MES (0/4); 40, RT (0/5) MES (0/5); 50, RT (0/5) MES (2/5); 60, RT (1/9) MES (6/9); 80, RT (0/9) MES (9/9); 100, RT (5/19) MES (18/19); 110, RT (2/5) MES (5/5); 120, RT (1/5) MES (5/5).

dl-cis-ML1078: 3, RT (0/5) MES (0/5); 10, RT (0/9) MES (3/9); 30, RT (1/9) MES (8/9); 60, RT (0/5) MES (5/5); 100, RT (3/9) MES (9/9); 110, RT (4/5) MES (5/5); 120, RT (10/10) MES (10/10); 160, RT (5/5) MES (5/5); 200, RT (5/5) MES (5/5).

dl-cis-ML1082: 3, RT (0/12) MES (0/12); 10, RT (0/11) MES (2/21); 30, RT (0/11) MES (12/21); 40, RT (0/5) MES (5/5); 60, RT (0/5) MES (14/15); 80, RT (5/5) MES (5/5); 100, RT (6/6) MES (15/16).

dl-trans-ML1096: 30, RT (0/10) MES (1/9); 100, RT (0/10) MES (3/10); 120, RT (0/5) MES (5/5); 150, RT (0/10) MES (7/10); 200, RT (8/20) MES (20/20); 205, RT (4/5) MES (4/5); 210, RT (4/5) MES (5/5); 220, RT (10/10) MES (10/10); 230, RT (5/5) MES (5/5); 270, RT (5/5) MES (5/5); 300, RT (8/8, 2 died) MES (8/8, 2 died).

ML1097: 3, RT (0/10) MES (0/10); 10, RT (0/10) MES (0/10); 30, RT (0/10) MES (0/10); 40, RT (0/5) MES (3/5); 60, RT (0/5) MES (4/5); 80, RT (0/5) MES (5/5); 100, RT (1/10) MES (9/10); 120, RT (3/5) MES (5/5); 150, RT (2/2) MES (2/2); 160, RT (4/5) MES (5/5); 180, RT (5/5) MES (5/5); 200, RT (9/10) MES (9/10).

dl-trans-ML1103: 30, RT (0/5) MES (0/5); 60, RT (0/5) MES (0/5); 100, RT (0/15) MES (13/15); 120, RT (0/5) MES (5/5); 140, RT (2/5) MES (5/5); 160, RT (0/1, 4 died) MES (1/1, 4 died); 180, RT (1/2, 3 died) MES (2/2, 3 died); 200, RT (4/4, 1 died) MES (4/4, 1 died).

CONCLUSION

The present invention is thus provided. Numerous adaptations and modifications can be effected by those skilled in the art within the spirit of this invention, the scope of which is particularly pointed out by the following distinctly claimed subject matter.

What is claimed is:

1. A method for ameliorating a generalized tonic clonic type epileptic seizure in a mammal comprising systemically administering to a mammal in need of treatment therefor a Benzothiazepine-compound in an amount effective to ameliorate said seizure, wherein the Benzothiazepine-compound is a benzothiazepine-type compound, or a pharmaceutically acceptable salt thereof, having calcium antagonist activity and which is represented by the following general formula:

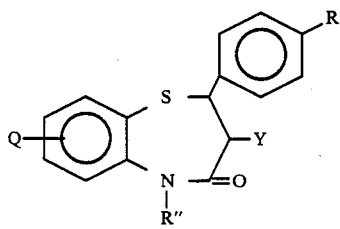

wherein
Q is hydro (H) or halo;
R is H, Lower alkoxy, lower haloalkyl, cyano, lower alkyl or halo;
Y is
OR', wherein R' is H of alkylacyl, provided that then there is full saturation between carbons 2 & 3 of the benzothiazepine nucleus and 2,3-dihydro-functionality thereat as well, or
Cl, provided that then there is ethylenic unsaturation between positions 2 & 3 of the ebenzothiazepine nucleus, and
R" is 2-[di(lower alkyl)amino]ethyl, 3-[di(lower alkyl)amino]propyl, 2-(pyrrolidino)ethyl, 3-(pyrrolidino)propyl, 2-(piperidino)ethyl, 3-(piperidino)propyl, 2-(morpholino)ethyl, 3-(morpholino)propyl or (N-pyridinium)alkyl with a suitable counterion being present,
provided that, in the cis-configuration, when Q is H or 8-Cl, R is methoxy, R' is acetyl, and R" is 2-(dimethylamino)-ethyl, then the compound is the levorotary isomer.

2. The method of claim 1, wherein the Benzothiazepine-compound is selected from the group consisting of 1-cis-DTZ, 1-cis-TA3090, M11014, ML1016, ML1017, ML1018, ML1020, ML1021, ML1048, ML1063, ML1064, ML1077, ML1078, ML1079, ML1082, ML1096, ML1097, ML1103, ML1104, and pharmaceutically acceptable salt(s) thereof, wherein each particular compound is identified as follows with respect to the formula (I):

| Compound | Q | R | Y: R' of OR' & C | R" |
|---|---|---|---|---|
| 1-cis-DTZ | H | OMe | acetyl | R"1a |
| 1-cis-TA3090 | 8-Cl | OMe | acetyl | R"1a |
| ML1014 | H | OMe | isovaleryl | R"1a |
| ML1016 | H | OMe | acetyl | R"1b |
| ML1017 | H | OMe | H | R"5 |
| ML1018 | H | OMe | acetyl | R"5 |
| ML1020 | H | OMe | H | R"3 |
| ML1021 | H | OMe | acetyl | R"3 |
| ML1048 | H | OMe | H | R"6 |
| ML1063 | H | OMe | H | R"7 |
| ML1064 | H | OMe | acetyl | R"7 |
| ML1077 | H | Cl | H | R"1a |
| ML1078 | H | CF3 | H | R"1a |
| ML1079 | H | Me | H | R"1a |
| ML1082 | H | CF3 | H | R"5 |
| ML1096 | 8-Cl | OMe | H | R"5 |
| ML1097 | H | OMe | *Cl | R"1a |
| ML1103 | H | OMe | H | R"5 |
| ML1104 | H | CN | H | R"5 | wherein also
with respect to Q, 8-Cl is 8-chloro;
with respect to R, OMe is methoxy; Cl is chloro; CF3 is trifluoromethyl; Me is methyl, and CN is cyano;
with respect to Y, *Cl indicates vinyl chloride at position 2, 3 of the benzothiazepine nucleus, and
with respect to R", R"1a is 2-(dimethylamino)ethyl; R"1b is 2-(diisopropylamino)ethyl; R"3 is 2-(pyrrolidino)ethyl; R"5 is 2-(piperidino)ethyl; R"6 is 3-(piperidino)propyl, and R"7 is 2-(morpholino)ethyl.

3. The method of claim 2, wherein the Benzothiazepine-compound is selected from the group consisting of ML11016, ML1017, ML1018, ML1021, ML1048, ML1077, ML1078, ML1103, and pharmaceutically acceptable salt(s) thereof.

4. The method of claim 2, wherein the Benzothiazephine-compound is selected from the group consisting of ML1021, ML1077, ML11078, ML1082, ML1096, and pharmaceutically acceptable salt(s) thereof.

5. The method of claim 2, wherein the Benzothiazephine-compound is selected from the group consisting of d-cis-ML1014, d-cis-ML1016, cis-ML1017, cis-ML1018, cis-ML1020, cis-MLI1021, cis-ML1048, cis-ML1063, cis-ML1064, cis-ML1077, cis-ML1078, cis-ML1079, cis-ML1082, trans-ML1096, trans-ML1103, cis-ML1104, and pharmaceutically acceptable salt(s) thereof.

6. The method of claim 2, wherein the Benzothiazephine-compound is selected from the group consisting of cis-ML1016, cis-ML1017, cis-ML1018, cis-ML1021, cis-ML1048, cis-ML1077, cis-ML1078, trans-ML1103, 11. The method of claim 2, wherein the Benzothiazepine-compound is 1-cis-DTZ, or a pharmaceutically acceptable salt thereof.

12. The method of claim 11, wherein the pharmaceutically acceptable salt is a hydrochloride salt.

13. The method of claim 2, wherein the Benzothiazepine-compound is ML1097, or a pharmaceutically acceptable salt thereof.

14. The method of claim 13, wherein the pharmaceutically acceptable salt is a hydrochloride salt.

15. The method of claim 1, wherein the Benzothiazepine-compound is selected from the group consisting of the following salts, identified as follows with respect to the formula (I):

| Compound | Q | R | Y: R' of OR' & C | R" | Salt |
| --- | --- | --- | --- | --- | --- |
| 1-cis-DTZ | H | OMe | acetyl | R"1a | HCl |
| 1-cis-TA3090 | 8-Cl | OMe | acetyl | R"1a | maleate |
| d-cis-ML1013 | H | OMe | valeryl | R"1a | fumerate |
| d-cis-ML1014 | H | OMe | isovaleryl | R"1a | fumerate |
| d-cis-ML1015 | H | OMe | pivalyl | R"1a | fumerate |
| d-cis-ML1016 | H | OMe | acetyl | R"1b | HCl |
| dl-cis-ML1017 | H | OMe | H | R"5 | HCl |
| dl-cis-ML1018 | H | OMe | acetyl | R"5 | HCl |
| dl-cis-ML1020 | H | OMe | H | R"3 | HCl |
| dl-cis-ML1021 | H | OMe | acetyl | R"3 | HCl |
| dl-cis-ML1047 | 8-Cl | OMe | pivalyl | R"1a | fumerate |
| dl-cis-ML1048 | H | OMe | H | R"6 | HCl |
| dl-cis-ML1063 | H | OMe | H | R"7 | HCl |
| dl-cis-ML1064 | H | OMe | acetyl | R"7 | HCl |
| dl-cis-ML1065 | H | OMe | H | +R"9a-X | Br/Cl |
| dl-cis-ML1066 | H | OMe | acetyl | +R"9a-X | Br/Cl |
| dl-cis-ML1077 | H | Cl | H | R"1a | HCl |
| dl-cis-ML1078 | H | CF3 | H | R"1a | HCl |
| dl-cis-ML1079 | H | Me | H | R"1a | HCl |
| dl-cis-ML1080 | H | OMe | adamantylcarboxy | R"1a | fumerate |
| dl-cis-ML1082 | H | CF3 | H | R"5 | HCl |
| dl-trans-ML1096 | 8-Cl | OMe | H | R"5 | HCl |
| ML1097 | H | OMe | *Cl | R"1a | HCl |
| dl-cis-ML1098 | H | H | H | R"5 | HCl |
| dl-trans-ML1103 | H | OMe | H | R"5 | HCl |
| dl-cis-ML1104 | H | CN | H | R"5 | HCl | and pharmaceutically acceptable salt(s) thereof.

7. The method of claim 2, wherein the Benzothiazephine-compound is selected from the group consisting of cis-ML1077, cis-ML1078, cis-ML1082, trans-ML1096, and pharmaceutically acceptable salt(s) thereof.

8. The method of claim 7, wherein the pharmaceutically acceptable salt is a hydrochloride salt.

9. The method of claim 2, wherein the Benzothiazephine-compound is 1-cis-TA3090, or a pharmaceutically acceptable salt thereof.

10. The method of claim 9, wherein the pharmaceutically acceptable salt is a maleate salt.

wherein also
with respect to Q, 8-Cl is 8-chloro;
with respect to R, OMe is methoxy; Cl is chloro; CF3 is trifluoromethyl; Me is methyl, and CN is cyano;
with respect to Y, *Cl indicates vinyl chloride at position 2,3 of the benzothiazepine nucleus, and
with respect to R", R"1a is 2-(dimethylamino)ethyl; R"1b is 2-(diisopropylamino)ethyl: R"3 is 2-(pyrrolidino)ethyl; R"5 is 2-(piperidino)ethyl; R"6 is 3-(piperidino)propyl; R"7 is 2-(morpholino)ethyl, and +R"9a-X is 2-(N-pyridinium)ethyl with a bromide and/or chloride counterion being present.

* * * * *